United States Patent
Givens, Jr.

(10) Patent No.: US 7,334,679 B2
(45) Date of Patent: Feb. 26, 2008

(54) TEAR OPEN PACKAGE FOR HYDROPHILIC-COATED CATHETER

(75) Inventor: William L. Givens, Jr., Lindenhurst, IL (US)

(73) Assignee: Hollister Incorporated, Libertyville, IL (US)

(*) Notice: Subject to any disclaimer, the term of this patent is extended or adjusted under 35 U.S.C. 154(b) by 223 days.

(21) Appl. No.: 11/079,877

(22) Filed: Mar. 14, 2005

(65) Prior Publication Data

US 2005/0199521 A1    Sep. 15, 2005

Related U.S. Application Data

(60) Provisional application No. 60/553,207, filed on Mar. 15, 2004.

(51) Int. Cl.
B65D 83/10    (2006.01)
A61B 17/06    (2006.01)

(52) U.S. Cl. .................. 206/364; 206/438; 383/209

(58) Field of Classification Search ........ 206/363–364, 206/438–440; 229/87.05; 383/200, 209
See application file for complete search history.

(56) References Cited

U.S. PATENT DOCUMENTS

| | | | |
|---|---|---|---|
| 2,353,746 A | | 7/1944 | Moore |
| 3,175,553 A | * | 3/1965 | Mattson ..................... 206/364 |
| 3,186,628 A | * | 6/1965 | Rohde ......................... 383/209 |
| 3,612,038 A | | 10/1971 | Halligan |
| 3,648,704 A | | 3/1972 | Jackson |
| 3,724,651 A | * | 4/1973 | Link ............................ 206/363 |
| 3,790,744 A | * | 2/1974 | Bowen ..................... 229/87.05 |
| 3,889,808 A | | 6/1975 | Helms |
| 3,926,309 A | * | 12/1975 | Center ........................ 206/364 |
| 3,967,728 A | | 7/1976 | Gordon et al. |
| 4,116,338 A | * | 9/1978 | Weichselbaum ............ 206/438 |
| 4,230,115 A | * | 10/1980 | Walz et al. ................. 206/364 |
| 4,290,526 A | | 9/1981 | Haiss |
| 4,364,478 A | | 12/1982 | Tüns |

(Continued)

FOREIGN PATENT DOCUMENTS

CH    677094    4/1994

(Continued)

*Primary Examiner*—Bryon P. Gehman
(74) *Attorney, Agent, or Firm*—Marshall, Gerstein & Borun LLP

(57) ABSTRACT

A tear open package for a catheter having an insertion end and a funnel end includes a pair of thin elongated sheets of gas impermeable material joined about their edges by a perimeter heat seal. The elongated sheets of material form a catheter-receiving cavity in which the catheter insertion end is near one end of the cavity and the funnel end is near the other end of the cavity. The perimeter heat seal includes at least an insertion end heat seal, a funnel end heat seal, and a pair of side heat seals which extend along each side of the package from the insertion end heat seal to the funnel end heat seal. The elongated sheets of material each include a tear line extending at least from one side of the package toward the other side of the package through at least one of the side heat seals. The tear lines extend between the catheter insertion end and the insertion end heat seal for opening at least the insertion end of the package by controlled tearing for removal and use of the catheter.

17 Claims, 5 Drawing Sheets

U.S. PATENT DOCUMENTS

| | | | |
|---|---|---|---|
| 4,379,506 A | 4/1983 | Davidson | |
| 4,629,447 A | 12/1986 | Stenzel | |
| 4,754,877 A | 7/1988 | Johansson et al. | |
| D300,947 S | 5/1989 | Utas Sjoberg | |
| 4,838,429 A | 6/1989 | Fabisiewicz et al. | |
| 4,863,016 A | 9/1989 | Fong et al. | |
| 4,889,523 A | 12/1989 | Sengewald | |
| 4,927,028 A | 5/1990 | Hemm et al. | |
| 4,993,555 A | 2/1991 | Hemm | |
| 5,165,540 A | 11/1992 | Forney | |
| 5,184,771 A | 2/1993 | Jud et al. | |
| 5,226,530 A | 7/1993 | Golden | |
| 5,356,068 A | 10/1994 | Moreno | |
| 5,372,254 A | 12/1994 | Gross | |
| 5,454,798 A | 10/1995 | Kubalak et al. | |
| 5,470,419 A | 11/1995 | Sasaki et al. | |
| 5,497,601 A | 3/1996 | Gonzalez | |
| 5,501,341 A | 3/1996 | Van Es | |
| 5,582,342 A | 12/1996 | Jud | |
| 5,836,697 A | 11/1998 | Chisea | |
| 5,895,374 A | 4/1999 | Rødsten | |
| 5,902,045 A * | 5/1999 | Resteghini | 383/209 |
| 6,004,305 A | 12/1999 | Hursman et al. | |
| 6,098,800 A | 8/2000 | Bennish, Jr. et al. | |
| 6,228,458 B1 | 5/2001 | Pinchen et al. | |
| 6,409,717 B1 | 6/2002 | Israelsson et al. | |
| 6,457,863 B1 | 10/2002 | Vassallo | |
| 6,578,709 B1 | 6/2003 | Kavanagh et al. | |
| 6,634,498 B2 | 10/2003 | Kayerød et al. | |
| 6,736,805 B2 * | 5/2004 | Israelsson et al. | 206/364 |
| 6,892,881 B2 | 5/2005 | Leitch | |
| 2003/0168365 A1 | 9/2003 | Kaern | |
| 2003/0174909 A1 | 9/2003 | Parra | |
| 2004/0136623 A1 | 7/2004 | Obara | |
| 2004/0142074 A1 | 7/2004 | Hentzel et al. | |
| 2005/0023180 A1 | 2/2005 | Intini | |

FOREIGN PATENT DOCUMENTS

| | | |
|---|---|---|
| EP | 0521618 A2 | 1/1993 |
| EP | 0677299 A1 | 10/1995 |
| EP | 0680896 B2 | 11/1995 |
| EP | 0909249 B1 | 4/1999 |
| EP | 0957043 A1 | 11/1999 |
| EP | 0959021 A1 | 11/1999 |
| EP | 1120355 A1 | 1/2001 |
| WO | WO 98/06642 | 2/1998 |
| WO | WO 01/52763 | 7/2001 |
| WO | WO 01/83316 | 11/2001 |
| WO | WO 03/064279 | 8/2003 |

* cited by examiner

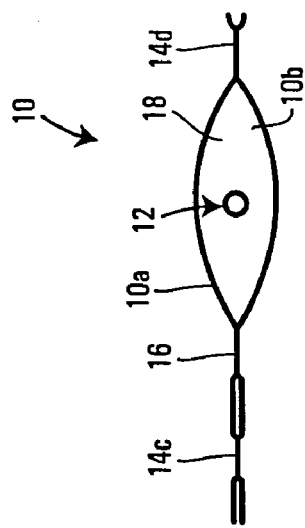
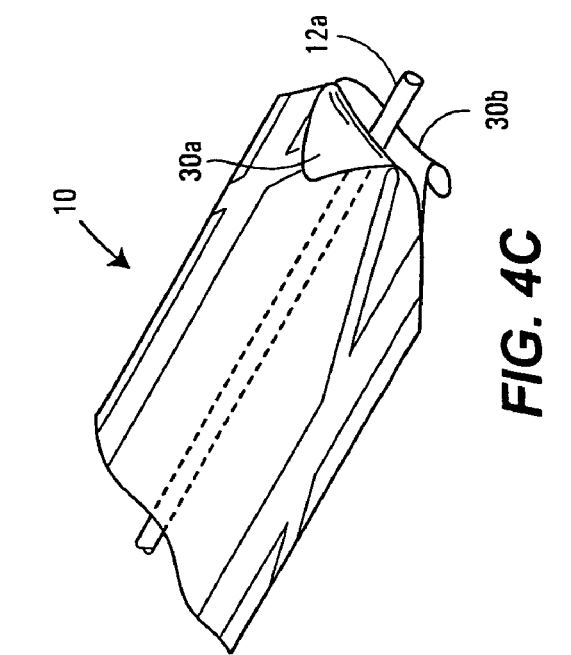
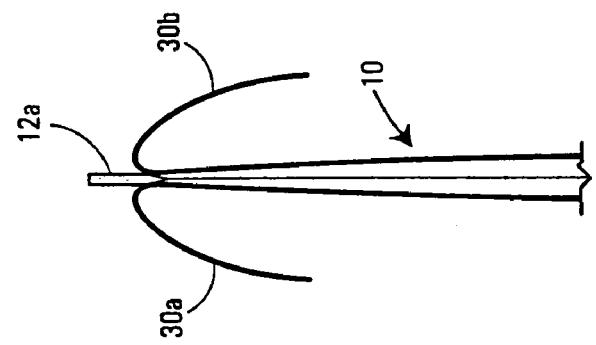
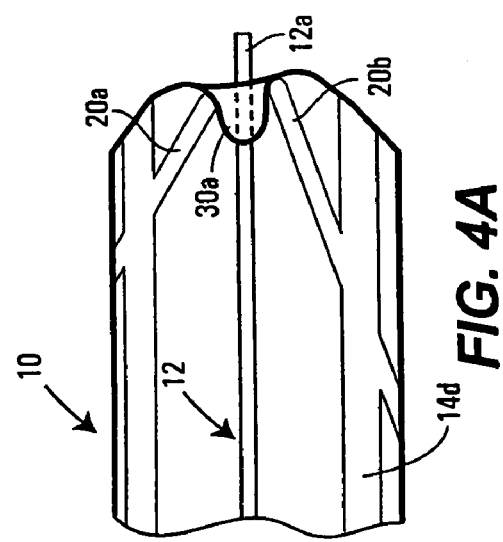

TEAR OPEN PACKAGE FOR HYDROPHILIC-COATED CATHETER

CROSS REFERENCE TO RELATED APPLICATION

This application claims priority from U.S. Provisional Patent Application Ser. No. 60/553,207 filed Mar. 15, 2004.

FIELD OF THE INVENTION

The present invention is generally directed to packages for catheters and, more particularly, a tear open package for a coated catheter.

BACKGROUND AND SUMMARY OF THE INVENTION

Current catheters are packaged in such a way that the user is usually required to touch the catheter in order to insert it. The present invention incorporates a controlled tearing line in a catheter package that leaves flaps that can be folded back after the catheter insertion end of the package is torn open to facilitate catheter insertion. In this manner, torn package edges are moved away from the insertion zone and, when extended, the catheter package becomes a urine-receiving sleeve.

Presently, there is significant interest in hydrophilic coated intermittent catheters that are packaged in a manner whereby they are completely ready-to-use as a result of vapor hydration when the catheter reaches the user. In order to accomplish this objective, the catheter's external packaging must be moisture vapor impermeable to maintain a 100 percent relative humidity atmosphere within the package cavity which holds the catheter. By utilizing a moisture vapor impermeable material, it is possible to ensure that the catheter is completely ready-to-use by confining the moisture vapor to the package to thereby prevent the catheter from drying out.

In the present invention, a controlled tearing line is used for opening the package while at the same time being able to utilize a suitably moisture vapor impermeable packaging material. The fact that this material is typically somewhat rigid presents a problem of potentially sharp edges that must not come into contact with the sensitive tissue around the urethra. Also, the controlled tearing line must not be characterized by any tendency to interfere with either the integrity of the sterility of the product or of the moisture vapor impermeability of the package.

In the present invention, the controlled tearing line is advantageously incorporated into the package by using laser scoring. Laser scoring maintains the integrity of product sterility as well as package moisture vapor impermeability by employing a process that utilizes a focused spot of energy to remove material to a specified or desired depth. The laser score lines provide controlled tear propagation while maintaining the package strength and barrier properties.

In order to remove the threat of injury from potentially sharp edges, the laser score lines are designed to leave foldable flaps near the insertion end of the catheter. These flaps can be folded back prior to catheter use to expose the tip of the catheter for insertion into the urethra by griping it through the package. Further, the laser score lines are also designed to cause an opening in the package at the funnel end of the catheter to allow the package to be used as a urine sleeve.

Other objects, advantages and features of the invention will become apparent from a consideration of the following specification taken in conjunction with the accompanying drawings.

BRIEF DESCRIPTION OF THE DRAWINGS

FIG. 2 is a cross-sectional view of the tear open package illustrated in FIG. 1 taken generally along the line 2-2;

FIG. 4A is a detailed plan view of the package of FIG. 3 with the chevron-shaped flaps folded back;

FIG. 4B is a side elevational view of the package of FIG. 4A with the chevron-shaped flaps folded back;

FIG. 4C is a perspective view of the package of FIG. 4A with the chevron-shaped flaps folded back;

DETAILED DESCRIPTION OF THE PREFERRED EMBODIMENTS

Figure 1:
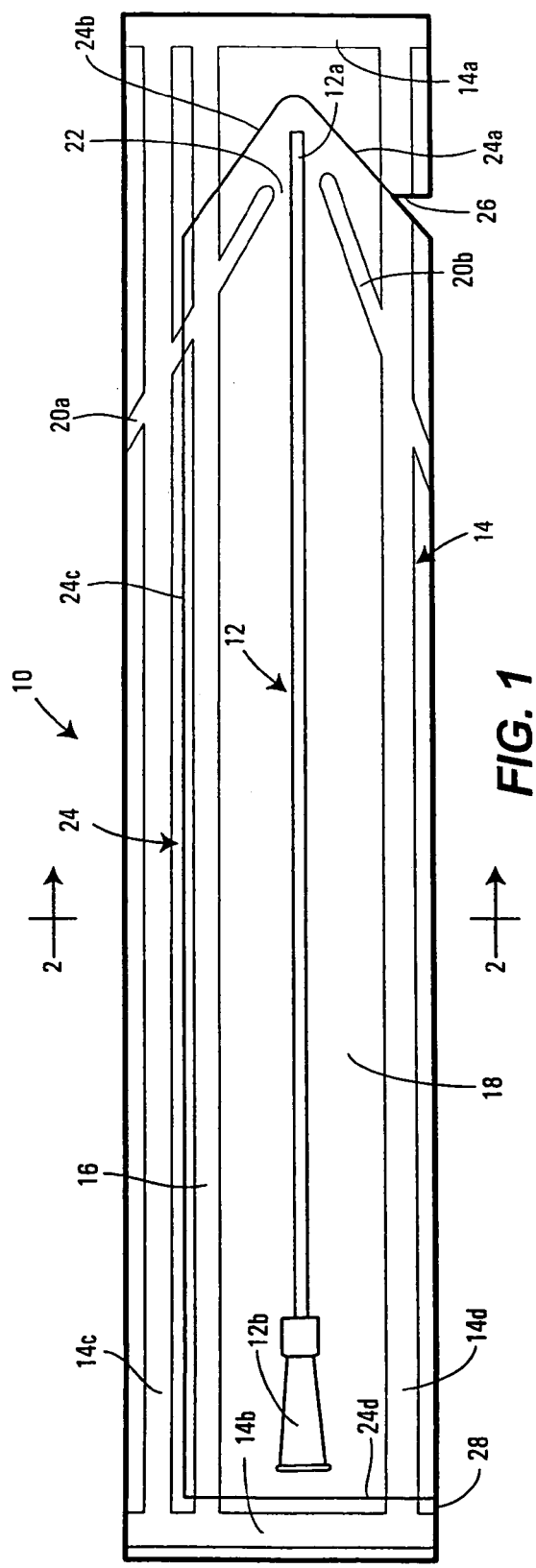
FIG. 1 is a top plan view of a tear open package for a coated catheter in accordance with the present invention.

Referring to FIG. 1, a tear-open package 10 for a catheter 12 is formed of a moisture vapor impermeable material. The moisture vapor impermeable material may comprise two thin sheets of a foil of a type already known for use in catheter packaging wherein the thin sheets are heat sealed to one another completely about the perimeter, but any other moisture vapor impermeable but flexible material having similar characteristics can be used. As will be appreciated from FIG. 1, the perimeter heat seal generally designated 14 includes heat seal portions 14a, 14b, 14c, and 14d.

More specifically, the perimeter heat seal 14 includes an end heat seal portion 14a at the insertion end 12a of the catheter 12, an end heat seal portion 14b at the funnel end of the catheter 12, and a pair of elongated side heat seal portions 14c and 14d extending generally parallel to the catheter 12, and it will also be seen that another heat seal 16 is provided. As will be appreciated, the heat seal 16 comprises an elongated interior heat seal that extends from the end heat seal portion 14a to the end heat seal portion 14b in generally parallel, closely spaced relation to the side heat seal portion 14c whereby the seal 16 cooperates with the end heat seal portions 14a and 14b and the side heat seal portion 14d to define a sealed catheter-receiving cavity 18.

Referring to FIG. 2 (which comprises a cross-section taken along the line 2-2 of FIG. 1), this will be better understood. The sealed catheter-receiving cavity 18 serves important functions; namely, it can house the hydrophilic catheter 12 in a moisture vapor atmosphere from the time the package 10 is sealed until the time it is opened by the user. It also ensures the catheter is ready to use and ensures the integrity of the sterility of the catheter 12.

In addition to the aforementioned seals 14 and 16, FIG. 1 illustrates that there are also chevron-shaped heat seals 20a and 20b. The chevron-shaped heat seals 20a, 20b angle inwardly from respective side heat seal portions 14c, 14d but terminate spaced from the end heat seal portion 14a to define a narrow passageway 22 through which the catheter 12 can extend. The catheter 12 extends through the narrow passageway defined by the chevron-shaped seals 20a, 20b where they are closest to the end heat seal portion 14a so the insertion end 12a of the catheter is at a point near the end heat seal portion 14a. In addition, the package 10 includes continuous laser score lines such as 24 about a substantial portion of the perimeter thereof.

Figure 3:
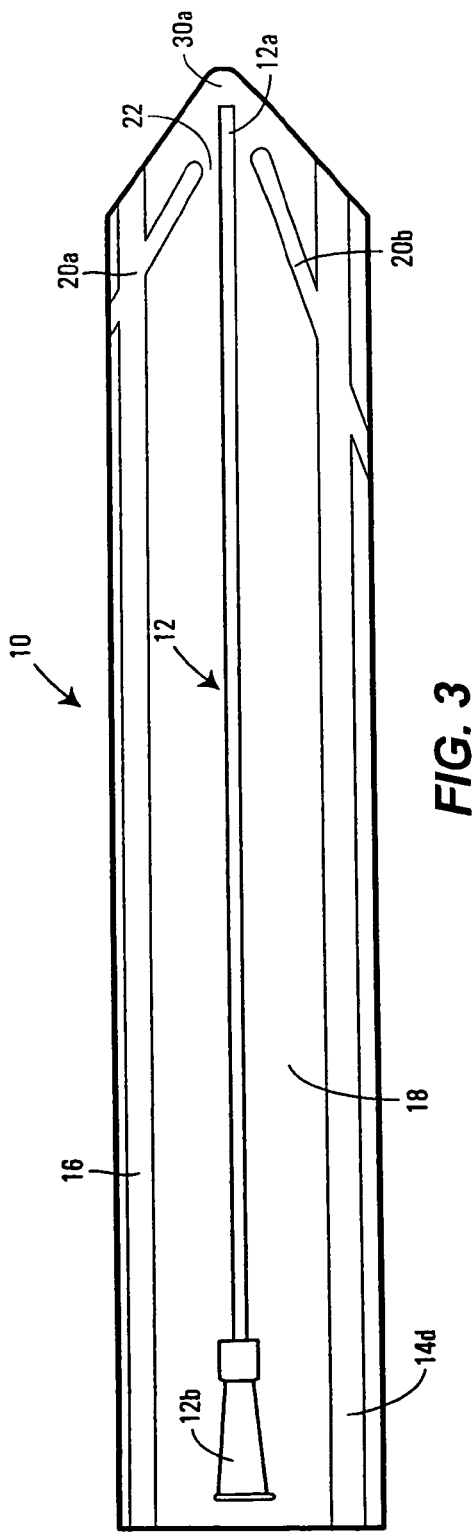
FIG. 3 is a top plan view of the package of FIG. 1 after it has been torn open for use of the coated catheter.

As will be appreciated, both of the sheets of foil are preferably scored so that the package 10 can be opened for use in the manner described below wherein a portion of both sheets is entirely removed as shown in FIG. 3.

In this connection, the two sheets of foil comprising the package 10 preferably each include a small cut-out as at 26 that is at the upstream end of its laser score line 24. The score lines such as 24 will be seen to extend from their upstream ends along a first insertion end laser score line portion such as 24a and then along a second insertion end laser score line portion such as 24b, wherein the second insertion end laser score line portions extend generally parallel to, but in spaced relation to, the corresponding chevron shaped-heat seal portions 20a and 20b. The laser score line portions such as 24a and 24b will be seen to be disposed between the chevron-shaped heat seal portions 20a and 20b and the end heat seal portion 14a.

As shown, the first and second insertion end laser score line portions such as 24a and 24b define a continuous curve where they are closest to the end heat seal portion 14a for a purpose that will become clear below.

Next, the laser score lines such as 24 will each include a side laser score line portion such as 24c that extends from the second insertion end laser score line portion such as 24b between and generally parallel to the side heat seal portion 14c and the interior heat seal 16 to a point short of the end heat seal portion 14b. Finally, the laser score lines such as 24 each include an end laser score line portion such as 24d that extends generally perpendicular from the side laser score line portion such as 24c inwardly of and generally parallel to the end heat seal portion 14b terminating at an end point 28 on the opposite edge of the package 10.

In other words, the end laser score line portions such as 24d each extend completely through the interior heat seal 16 and the side heat seal portion 14d.

With this construction, it will be appreciated that the laser score lines such as 24 can be utilized in a unique manner to prepare the package 10 and the catheter 12 for use in a sterile manner. The user grips the package as at 26 to initiate a controlled tear along the laser score lines such as 24 near the insertion end 12a of the catheter 12 and then proceeds with the controlled tear through both sheets of foil by following the laser score lines such as 24 along, and in the order of, the laser score line portions such as 24a, 24b, 24c, and 24d all the way around the catheter 12 to the end point 28 to complete opening of the package 10. As shown in FIGS. 4a, 4b, and 4c, this forms two chevron-shaped flaps 30a and 30b from the two thin sheets of foil that extend beyond and cover the insertion end 12a of the catheter 12.

In addition, the opposite end of the package 10 adjacent the funnel 12b of the catheter 12 will be open as a result of severing the package inwardly of the end heat seal portion 14b. In other words, the cavity 18 is open at both ends, i.e., at the insertion end 12a of the catheter 12 and adjacent the funnel 12b of the catheter 12, after the laser score lines such as 24 have been used as described above to open the package 10. However, both ends of the catheter 12 will still be covered by the remaining portions of the package 10 which assists in maintaining the sterility of the catheter (see FIG. 3).

As shown in FIGS. 4a, 4b, and 4c, the flaps 30a and 30b can be gripped by the user and folded back past the insertion end 12a of the catheter 12 to expose the tip for insertion without touching the catheter. The flaps 30a and 30b will be folded back generally to the narrow passageway 22 defined by the chevron-shaped heat seal portions 20a and 20b to expose only the catheter tip. When this has been done, the catheter 12 can be inserted up to a point approaching where the flaps 30a and 30b have been folded back while gripping the catheter 12 through the package 10.

Specifically, the catheter 12 can be gripped through the portions of the package 10 remaining after using the laser score lines such as 24 to open it. This provides the user with a good grip which is important where there is a lubricious coating. As is known, the coating which is found, e.g., on a ready to use hydrophilic intermittent catheter, is highly lubricious and, thus, difficult to handle.

Moreover, it is important to eliminate the need to handle the lubricious coating found on ready-to-use hydrophilic intermittent catheters for yet another reason; namely, to eliminate the risk of contamination that comes from handling the catheter directly which can lead to urinary tract infections.

Figure 5:
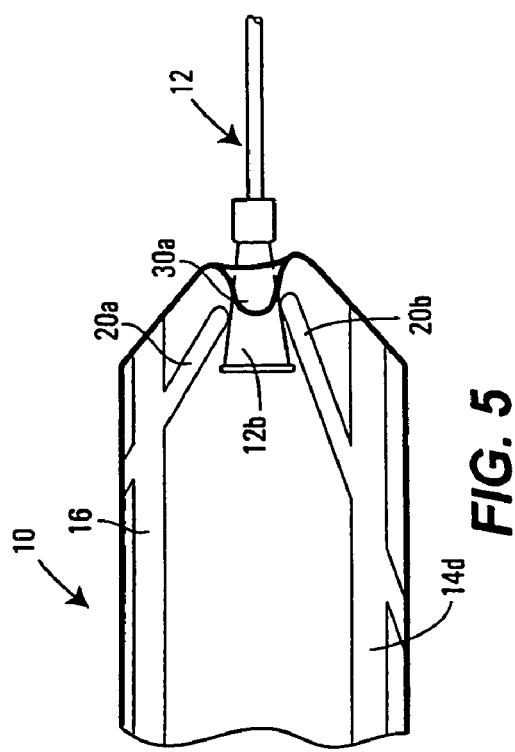
FIG. 5 is a detailed plan view similar to FIG. 4A with the catheter fully extended within the tear open package.

After the catheter 12 has been inserted up to a point approaching where the flaps 30a and 30b have been folded back, the entire remaining portion of the package 10 can be slid further toward the funnel 12b to expose more of the catheter 12 for insertion. Then, the catheter 12 can be re-gripped through the remaining portion of the package 10 for further insertion. By repeating this process, the catheter 12 can be fully inserted, and the chevron-shaped heat seal portions 20a and 20b will stop the package 10 from sliding beyond the funnel 12b on the catheter 12 which permits the package to be used as a urine sleeve for the catheter (see FIG. 5).

Figure 6:
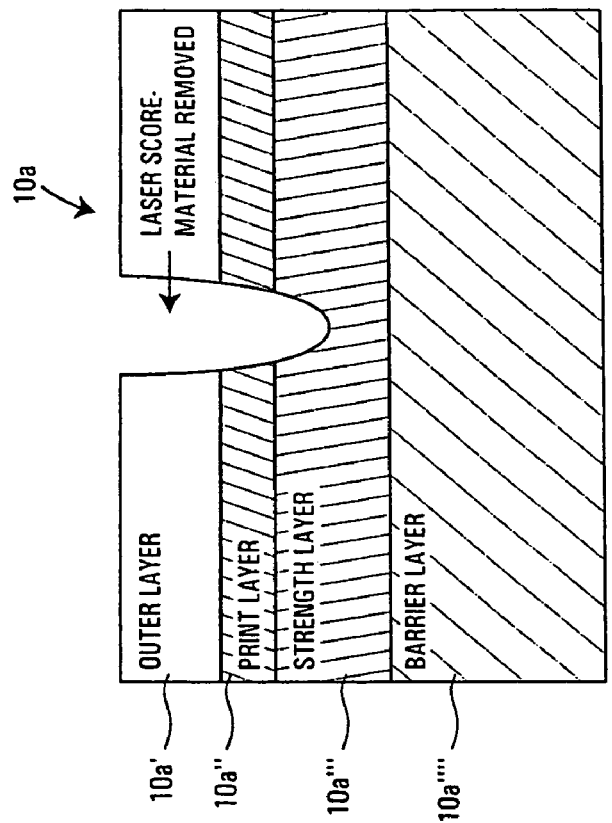
FIG. 6 is a schematic view of laser scoring of a gas impermeable material for use in the tear open package.

Referring to FIGS. 2 and 6, the material for the package 10 can comprise two thin sheets of foil 10a and 10b which can be heat sealed and include an outer layer, a print layer, a strength layer, and a barrier layer. Each sheet of thin foil 10a and 10b can be laser scored completely through the outer layer such as 10a' and the print layer such as 10a'' and partially through the strength layer such as 10a''' so the barrier layer such as 10a'''' can completely fulfill its function of maintaining moisture vapor impermeability to ensure, in the case of a hydrophilic intermittent catheter, that the surface coating does not dry out so the catheter is ready-to-use upon opening the package. At the same time, the laser scoring provides a controlled tear line that requires little effort by the user to impart controlled tear propagation for opening the package as described in detail above.

In one embodiment, the thin sheets of foil 10a and 10b may comprise a product sold by Smurfit Flexible Packaging, 1228 E. Tower Rd., Schaumburg, Ill. 60173 as Item # TS303201, and it may have thicknesses of 0.50 mil for the outer layer 10a', 0.10 mil for the print layer 10a'', 0.625 mil for the strength layer 10a''', and 1.75 mil for the barrier layer 10a''''.

Figure 7:
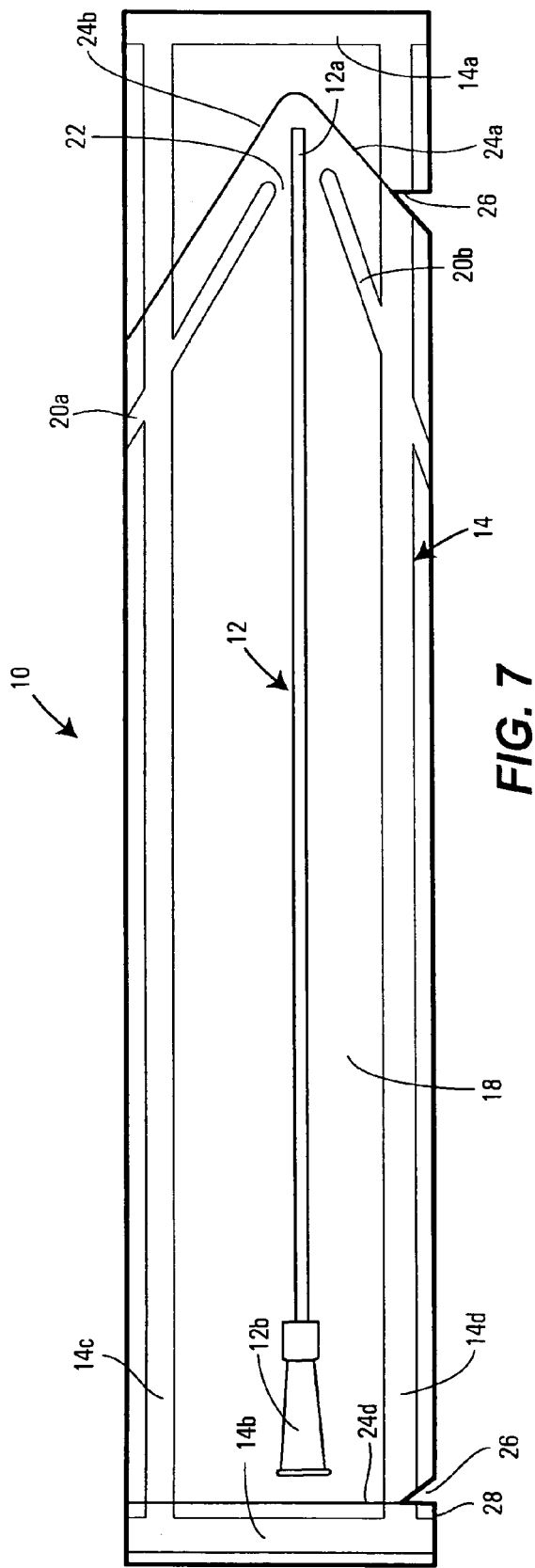
FIG. 7 is a top plan view of another embodiment of tear open package for a coated catheter in accordance with the invention.

In the embodiment shown in FIG. 7, the laser scoring can be provided in a pattern that differs from what is illustrated in FIGS. 1 and 2. The laser score line 24c can be entirely eliminated in which case the interior heat seal 16 can also be eliminated and the laser score lines 24b and 24d can be made to extend through the side heat seal portion 14c. With this arrangement, it will be appreciated that the opposite ends of the package 10 can be separately opened by the user.

As shown in FIG. 7, the two sheets of foil comprising the package 10 preferably each include a small cut-out as at 26 that is at the upstream end of laser score line 24a as well as at the upstream end of the laser score line 24d to facilitate opening the opposite ends of the package 10.

Figure 8:
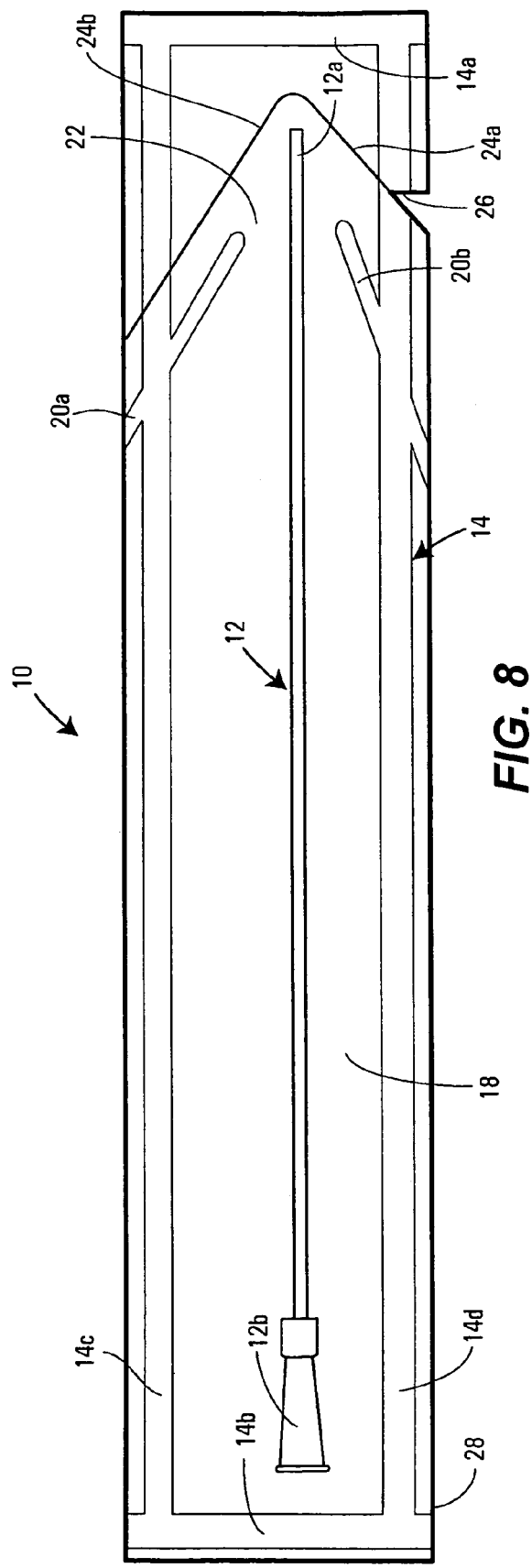
FIG. 8 is a top plan view of yet another embodiment of tear open package for a coated catheter in accordance with the present invention.

In the embodiment shown in FIG. 8, the laser score lines 24c and 24d can be eliminated and optionally (not shown) the heat seal portions 20a and 20b can be eliminated. If retained, the heat seal portions 20a and 20b will define a wider passageway 22 between them greater than the width of the funnel 12b so as to permit the complete removal of the catheter 12 from the package 10. In either case, the interior heat seal 16 can be entirely eliminated and the laser score line 24b can be made to extend completely through the side heat seal portion 14c as shown.

In this embodiment, it will be appreciated that the user will be able to open only the end of the package 10 adjacent the insertion end 12a of the catheter 12.

After the package 10 has been opened by the user adjacent the insertion end 12a of the catheter 12, and the user has used the package to grip and insert the catheter 12, the user can completely remove the package 10 from the catheter 12 and discard it rather than using the package as a urine sleeve.

As will be appreciated, the present invention addresses the problem of adding a "no-touch" feature to a catheter while maintaining the integrity of the catheter package. Moreover, it accomplishes this without incurring any risk of rough or sharp edges being presented to the sensitive tissue around the urethra while permitting the catheter package to be used as a urine sleeve.

As for the advantages of the invention, they include (i) providing a "no-touch" feature that accommodates easier insertion for catheters that are characterized by a lubricious coating, (ii) providing a "no-touch" feature that serves to prevent the possibility of issues that arise from catheter contamination from user handling, (iii) providing a catheter that can be hydrated before it reaches the user so it is completely ready-to-use without the need to provide a hydrating medium after opening a catheter package, (iv) providing a package that is easily opened by the user without the need for utilizing either scissors or a knife in a manner that protects the integrity of the package, and (v) providing controlled tear propagation to produce flaps at the insertion end of the package wherein the potentially sharp edges of the package are folded away from the urethra prior to use to avoid the risk of injury.

While the package is highly advantageous for hydrophilic intermittent catheters, and in particular hydrophilic coated intermittent catheters that have been activated by vapor hydration, the package is equally well suited for any other medical device or item that can benefit from a no-touch feature including, but not limited to other catheter embodiments such as a jelled catheter.

While preferred embodiments of the invention have been set forth in detail in the foregoing, it will be appreciated that the details herein given may be varied by those skilled in the art without departing from the true spirit and scope of the appended claims.

What is claimed is:

1. A tear open package, for a hydrophilic catheter having an insertion end and a funnel end, comprising:
    a pair of thin elongated sheets of gas impermeable material joined about their edges by a perimeter heat seal, the elongated sheets of material defining an elongated cavity receiving a catheter therein, the catheter having the insertion end near one end of the cavity and the funnel end near the other end of the cavity;
    the perimeter heat seal including at least an insertion end heat seal portion at one end of the package, a funnel end heat seal portion at the other end of the package, and a pair of side heat seal portions along each side of the package each extending from the insertion end heat seal portion to the funnel end heat seal portion in spaced relation to one another; and
    a respective tear line in each of the elongated sheets of material extending in registration with one another from one side of the package toward the other between the insertion end of the catheter and the insertion end heat seal portion, the tear lines extending through at least one of the side heat seal portions for opening the package by controlled tearing along the tear lines, the tear lines in the elongated sheets of material being formed into a first insertion end tear line portion and a second insertion end tear line portion to define respective continuous chevron-shaped insertion end tear lines.

2. The tear open package of claim 1 wherein the continuous chevron-shaped insertion end tear lines project toward and define a continuous curve at a point nearest to the insertion end heat seal portion.

3. A tear open package, for a hydrophilic catheter having an insertion end and a funnel end, comprising:
    a pair of thin elongated sheets of gas impermeable material joined about their edges by a perimeter heat seal, the elongated sheets of material defining an elongated cavity receiving a catheter therein, the catheter having the insertion end near one end of the cavity and the funnel end near the other end of the cavity;
    the perimeter heat seal including at least an insertion end heat seal portion at one end of the package, a funnel end heat seal portion at the other end of the package, and a pair of side heat seal portions along each side of the package each extending from the insertion end heat seal portion to the funnel end heat seal portion in spaced relation to one another;
    a respective chevron-shaped insertion end heat seal portion angling inwardly from each of the side heat seal portions in a direction generally toward the insertion end heat seal portion, the chevron-shaped heat seal portions terminating near but in spaced relation to the insertion end heat seal portion to form a narrow passageway for the insertion end of the catheter; and
    a respective tear line in each of the elongated sheets of material extending in registration with one another from one side of the package toward the other between the insertion end of the catheter and the insertion end heat seal portion, the tear lines extending through at least one of the side heat seal portions for opening the package by controlled tearing along the tear lines, the tear lines in the elongated sheets of material being formed into a first insertion end tear line portion and a second insertion end tear line portion to define respective continuous chevron-shaped insertion end tear lines.

4. The tear open package of claim 3 wherein the continuous chevron-shaped insertion end tear lines are located generally between the chevron-shaped heat seal portions and the insertion end heat seal portion.

5. The tear open package of claim 4 wherein the continuous chevron-shaped insertion end tear lines define a generally continuous curve at the point where they are closest to the insertion end heat seal portion.

6. A tear open package, for a hydrophilic catheter having an insertion end and a funnel end, comprising:
    a pair of thin elongated sheets of gas impermeable material joined about their edges by a perimeter heat seal, the elongated sheets of material defining an elongated cavity receiving a catheter therein, the catheter having the insertion end near one end of the cavity and the funnel end near the other end of the cavity;

the perimeter heat seal including at least an insertion end heat seal portion at one end of the package, a funnel end heat seal portion at the other end of the package and first and second side heat seal portions along first and second sides of the package each extending from the insertion end heat seal portion to the funnel end heat seal portion in spaced relation to one another;

an elongated interior heat seal extending from the insertion end heat seal portion to the funnel end heat seal portion in closely spaced parallel relation to one of the first and second side heat seal portions;

a respective chevron-shaped insertion end heat seal portion angling inwardly from each of the first and second side heat seal portions toward the insertion end heat seal portion and terminating in spaced relation to the insertion end heat seal portion and to each other to define a narrow passageway therebetween; and a respective tear line in each of the elongated sheets of material extending in registration with one another from one side of the package toward the other between the insertion end of the catheter and the insertion end heat seal portion, the tear lines extending through the other of the first and second side heat seal portions and the elongated interior heat seal for opening the package adjacent the insertion end of the catheter by controlled tearing along the tear lines, the tear lines in the elongated sheets of material being formed into a first insertion end tear line portion and a second insertion end tear line portion to thereby define respective continuous chevron-shaped insertion end tear lines.

7. The tear open package of claim 6 wherein the continuous chevron-shaped insertion end tear lines are located generally between the chevron-shaped heat seal portions and the insertion end heat seal portion.

8. The tear open package of claim 7 wherein the continuous chevron-shaped insertion end tear lines define a generally continuous curve at the point where they are closest to the insertion end heat seal portion.

9. The tear open package of claim 7 including a side tear line in each of the elongated sheets of material extending from the continuous chevron-shaped insertion end tear lines toward the end heat seal portion.

10. The tear open package of claim 9 wherein the side tear lines extend between and parallel to the elongated interior heat seal and the one of the first and second side heat seal portions to near the end heat seal portion.

11. The tear open package of claim 9 including an end tear line in each of the elongated sheets of material extending from the side tear line inwardly of and generally parallel to the end heat seal portion.

12. The tear open package of claim 11 wherein the end tear lines extend completely through the elongated interior heat seal and the other of the first and second side heat seal portions.

13. The tear open package of claim 12 wherein the continuous chevron-shaped insertion end tear lines, the side tear lines, and the end tear lines form a continuous tear line in each of the elongated sheets of material.

14. A tear open package, for a hydrophilic catheter having an insertion end and a funnel end, comprising:

a pair of thin elongated sheets of gas impermeable material joined about their edges by a perimeter heat seal, the elongated sheets of material defining an elongated cavity receiving a catheter therein, the catheter having the insertion end near one end of the cavity and the funnel end near the other end of the cavity;

the perimeter heat seal including at least an insertion end heat seal portion at one end of the package, a funnel end heat seal portion at the other end of the package and first and second side heat seal portions along first and second sides of the package each extending from the insertion end heat seal portion to the funnel end heat seal portion in spaced relation to one another;

an elongated interior heat seal extending from the insertion end heat seal portion to the funnel end heat seal portion in closely spaced parallel relation to one of the first and second side heat seal portions;

a respective chevron-shaped heat seal portion angling inwardly from each of the first and second side heat seal portions toward the insertion end heat seal portion and terminating in spaced relation to the insertion end heat seal portion and to each other to define a narrow passageway therebetween; and a respective continuous tear line in each of the elongated sheets of material in registration with one another and extending from a cutout in one side of the package toward the other side of the package between the insertion end of the catheter and the insertion end heat seal portion, and then extending generally parallel to and closely spaced from the other side of the package, and then extending back to the one side of the package between the funnel end of the catheter and the funnel end heat seal portion to an end point to open the cavity for the catheter adjacent both the insertion end and the funnel end while still covering the catheter;

the portions of the continuous tear lines extending generally parallel to and closely spaced from the other side of the package being disposed between the elongated interior heat seal portion and the one of the first and second side heat seal portions;

whereby the package is opened starting at the cutout in the one side of the package and continuing to the end point in the one side of the package by controlled tearing along the tear lines.

15. The tear open package of claim 14 wherein the portions of the continuous tear lines near the insertion end heat seal portion are continuous chevron-shaped tear lines, the chevron-shaped tear lines being located generally between the chevron-shaped heat seal portions and the insertion end heat seal portion, the chevron-shaped tear lines being curved at the point nearest the insertion end heat seal portion.

16. The tear open package of claim 15 wherein the chevron-shaped tear lines form chevron-shaped foldable flaps, the insertion end of the catheter extending through the narrow passageway defined by the chevron-shaped heat seal portions, the chevron-shaped flaps being foldable back past the insertion end of the catheter to the narrow passageway to expose the insertion end thereof.

17. The tear open package of claim 15 wherein the elongated sheets of material comprise foil having an outer layer, a print layer, a strength layer, and a barrier layer, and the tear lines are formed in each of the elongated sheets of material by laser scoring completely through the outer layer and the print layer and by laser scoring partially through the strength layer without penetrating the barrier layer.

* * * * *